(12) United States Patent
Peppi et al.

(10) Patent No.: US 12,296,126 B2
(45) Date of Patent: May 13, 2025

(54) WEARABLE MICROPUMP FOR THERAPEUTIC DRUG DELIVERY

(71) Applicant: The Charles Stark Draper Laboratory, Inc., Cambridge, MA (US)

(72) Inventors: Marcello Peppi, Medford, MA (US); Ernest Soonho Kim, Cambridge, MA (US)

(73) Assignee: The Charles Stark Draper Laboratory, Inc.

( * ) Notice: Subject to any disclaimer, the term of this patent is extended or adjusted under 35 U.S.C. 154(b) by 96 days.

(21) Appl. No.: 18/120,286

(22) Filed: Mar. 10, 2023

(65) Prior Publication Data

US 2023/0211137 A1    Jul. 6, 2023

Related U.S. Application Data

(63) Continuation of application No. 16/581,153, filed on Sep. 24, 2019, now Pat. No. 11,602,622.

(51) Int. Cl.
*A61M 31/00* (2006.01)
*A61M 5/142* (2006.01)
*A61M 5/145* (2006.01)

(52) U.S. Cl.
CPC ...... *A61M 31/002* (2013.01); *A61M 5/14276* (2013.01); *A61M 5/14228* (2013.01); *A61M 2005/14513* (2013.01); *A61M 5/1452* (2013.01); *A61M 2205/3553* (2013.01); *A61M 2205/502* (2013.01); *A61M 2209/088* (2013.01); *A61M 2210/0612* (2013.01); *A61M 2210/0625* (2013.01); *A61M 2210/0662* (2013.01); *A61M 2210/1003* (2013.01); *A61M 2210/1067* (2013.01); *A61M 2210/1078* (2013.01); *A61M 2210/1433* (2013.01)

(58) Field of Classification Search
CPC .............. A61M 31/002; A61M 5/1452; A61M 2205/502; A61M 2209/088; A61M 2210/0662

See application file for complete search history.

(56) References Cited

U.S. PATENT DOCUMENTS

| 10,449,294 | B1 | 10/2019 | Estes |
| 2004/0220552 | A1 | 11/2004 | Heruth et al. |
| 2005/0137579 | A1 | 6/2005 | Heruth et al. |
| 2005/0277882 | A1 | 12/2005 | Kriesel |
| 2009/0292247 | A1 | 11/2009 | Basso et al. |
| 2013/0053823 | A1* | 2/2013 | Fiering ............... A61M 31/002 604/246 |

(Continued)

OTHER PUBLICATIONS

Medtronic, "SynchroMed II Drug Infusion Pump," retrieved from https://www.medtronic.com/us-en/healthcare-professionals/products/neurological/intrathecal-baclofen-theraphy-systems/synchromed-ii.html (Year: 2019).

(Continued)

*Primary Examiner* — Bradley J Osinski
(74) *Attorney, Agent, or Firm* — Foley & Lardner LLP

(57) ABSTRACT

The present disclosure describes a system for the delivery of therapeutic substances to the cavities of a patient. The system can include a wearable micropump that is fluidically coupled with a handpiece. The handpiece can be inserted, for example, into the middle ear via a surgical tympanotomy approach. The system can enable a controlled injection of a therapeutic substance directly into the patient's cavity.

13 Claims, 4 Drawing Sheets

(56) References Cited

U.S. PATENT DOCUMENTS

2015/0265824 A1 9/2015 Lalwani et al.
2019/0022397 A1 1/2019 Srivastava et al.

OTHER PUBLICATIONS

US Final Office Action on U.S. Appl. No. 16/581,153 dated Jul. 14, 2022 (16 pages).
US Non-Final Office Action on U.S. Appl. No. 16/581,153 dated Jan. 19, 2022 (15 pages).
US Notice of Allowance on U.S. Appl. No. 16/581,153 dated Nov. 2, 2022 (7 pages).

* cited by examiner

WEARABLE MICROPUMP FOR THERAPEUTIC DRUG DELIVERY

CROSS-REFERENCE TO RELATED APPLICATIONS

The present application is a continuation of U.S. patent application Ser. No. 16/581,153, filed Sep. 24, 2019, the disclosure of which is incorporated herein by reference in its entirety.

BACKGROUND OF THE DISCLOSURE

Delivery of therapeutics to the human inner ear can be challenging for clinicians. Two anatomic "windows" from the middle ear to the inner ear exist, the oval and round windows. Each of these windows include a semi-permeable membrane. Drug delivery to the inner ear requires that a therapeutic substance cross one of these membranes.

SUMMARY OF THE DISCLOSURE

Inner ear drug delivery can use diffusion to cross one or both of the membranes of the anatomic windows to the inner ear. Relying on diffusion across a membrane poses a number of difficulties. For example, diffusing therapeutic substances across the membranes can introduce a lack of precision in terms of dose delivery. Relying on diffusion can also limit the size and characteristics of therapeutic substance's molecules because, for example, not all substances can diffuse across the membranes. Another example challenge is that the round window membrane permeability can vary between patients or during states of inflammation. The handpiece of the present disclosure can overcome these challenges by delivering a therapeutic substance directly to the inner ear.

According to at least one aspect of the disclosure, a fluid delivery system includes a handpiece. The handpiece includes a tool shaft including a first portion of a microfluidic channel. The handpiece can include an end of the shaft of the handpiece that is connectable to a tubing to receive fluid into the one or more microfluidic channels via the tubing. The other end of the shaft of the handpiece includes a tip of the shaft including an outlet projectable into a cavity of patient to deliver fluid from the one or more microfluidic channels to the patient. The system can include a wearable micropump. The micropump can include a housing including one or more attachments. The wearable micropump can include a first reservoir configured to hold a first fluid. The wearable micropump can include a first pump configured to flow the first fluid from the first reservoir through a port to a tubing connectable to the port. The wearable pump can include one or more processors configured to cause the pump to deliver the fluid through the tubing to an outlet connected via the tubing based on one or more settings that are settable during delivery of the fluid via the outlet into the cavity of the patient.

In some implementations, the wearable micropump can include a stabilization unit to counteract a movement of a limb on which the wearable micropump is worn. The wearable micropump can include a strap to couple the wearable micropump with the wrist of a user. The wearable micropump can include a second reservoir configured to hold a second fluid.

The system can include a tubing fluidically coupling the wearable micropump with the handpiece. The tubing can include a dead volume of between about 1 microliter to 75 microliters. In some implementations, the first reservoir can include a pierceable septum to inject the first fluid into the first reservoir. The first reservoir can be removable from the wearable micropump. In some implementations, the first pump can be a lead screw-driven mini syringe pump, a 3-actuator micropump, a mini peristaltic pump, or a pneumatic/hydraulic-driven pump. In some implementations, the collar can be configured to seat with a round window of a patient's cochlea.

According to at least one aspect of the disclosure, a wearable micropump includes a housing, a reservoir, a pump, and one or more processors. The housing includes one or more attachments. The reservoir is configured to hold a fluid. The pump is configured to flow the fluid from the reservoir through a port to a tubing connectable to the port. The one or more processors are configured to cause the pump to deliver the fluid through the tubing to an outlet connected via the tubing based on one or more settings that are settable during delivery of the fluid via the outlet.

According to at least one aspect of the disclosure, a method for delivering a drug can include providing a wearable micropump system. The system can include a handpiece and a wearable micropump. The method for delivering a fluid or drug to a patient can include establishing a fluidic coupling between a wearable micropump and a handpiece tool via a tubing connected between a port of the wearable micropump and an end of a shaft of the handpiece tool having a microfluidic channel. The wearable micropump, which can be worn by a wearer, can include a reservoir configured to hold a fluid and a pump configured to flow the fluid from the reservoir through a port connectable to the tubing. The handpiece tool can include a tip of the shaft of the handpiece tool. The tip of the shaft of the handpiece tool can include inserting, by the wearer, into a cavity of a patient. The wearable micropump responsive to the pump and while being worn by the wearer, can include delivering fluid from the reservoir through the tubing through the microfluidic channel of the handpiece tool through an outlet of the tip of the handpiece tool to the cavity of the patient.

In some implementations, the method can include stabilizing, with a stabilization unit of the wearable micropump, a movement of a limb on which the wearable micropump is worn. The method can include flowing the first fluid from the first reservoir and the second fluid from the second reservoir into the handheld device. In some implementations, the method can include seating the collar in the round window. In some implementations, the method can include withdrawing a fluid from the cochlea with a second pump of the wearable micropump.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

The various concepts introduced above and discussed in greater detail below may be implemented in any of numerous ways as the described concepts are not limited to any particular manner of implementation. Examples of specific implementations and applications are provided primarily for illustrative purposes.

The present disclosure discusses a drug delivery system. The system can be a two part system that can include a delivery component, such as a handpiece, and a wearable micropump. The micropump can be worn on the user's wrist or arm while the user injects a therapeutic substance or other fluid into a cavity of the patient. Bringing the micropump close to the point of insertion (e.g., placing the micropump on the user's wrist) can improve the precision of drug penetration and drug diffusion while reducing the amount of dead volume between the pump and the handpiece and also reducing the fluid resistance along the injection path. Reducing the fluid resistance can decrease the chance of failure because the system can be operated under lower pressure. Also, a wearable micropump can enable higher control of the handpiece when compared to a handpiece with a built in pump which can be top heavy and bulky. The system can include multiple reservoirs that can be loaded with different drugs for simultaneous or sequential delivery to the patient. The micropump is configured to be wearable to enable ergonomic use of the system and to leave the user's hands free to perform other tasks during the injection of the fluid.

The system can be used to deliver drugs to a cavity within the patient. For example, the handpiece can be inserted into the middle ear via a surgical tympanotomy approach. The handpiece can enable a controlled injection of a therapeutic substance directly through the round window membrane and into the inner ear. The direct delivery of the therapeutic substance to the inner ear can enable the delivery of a precise amount of therapeutic substance into the inner ear. Because the therapeutic substance is delivered directly to the inner ear, the delivery of the therapeutic substance is not subject to limitations on molecule size and inconsistent diffusion rates that are present when therapeutic substances are diffused across the round window membrane.

Figure 1:
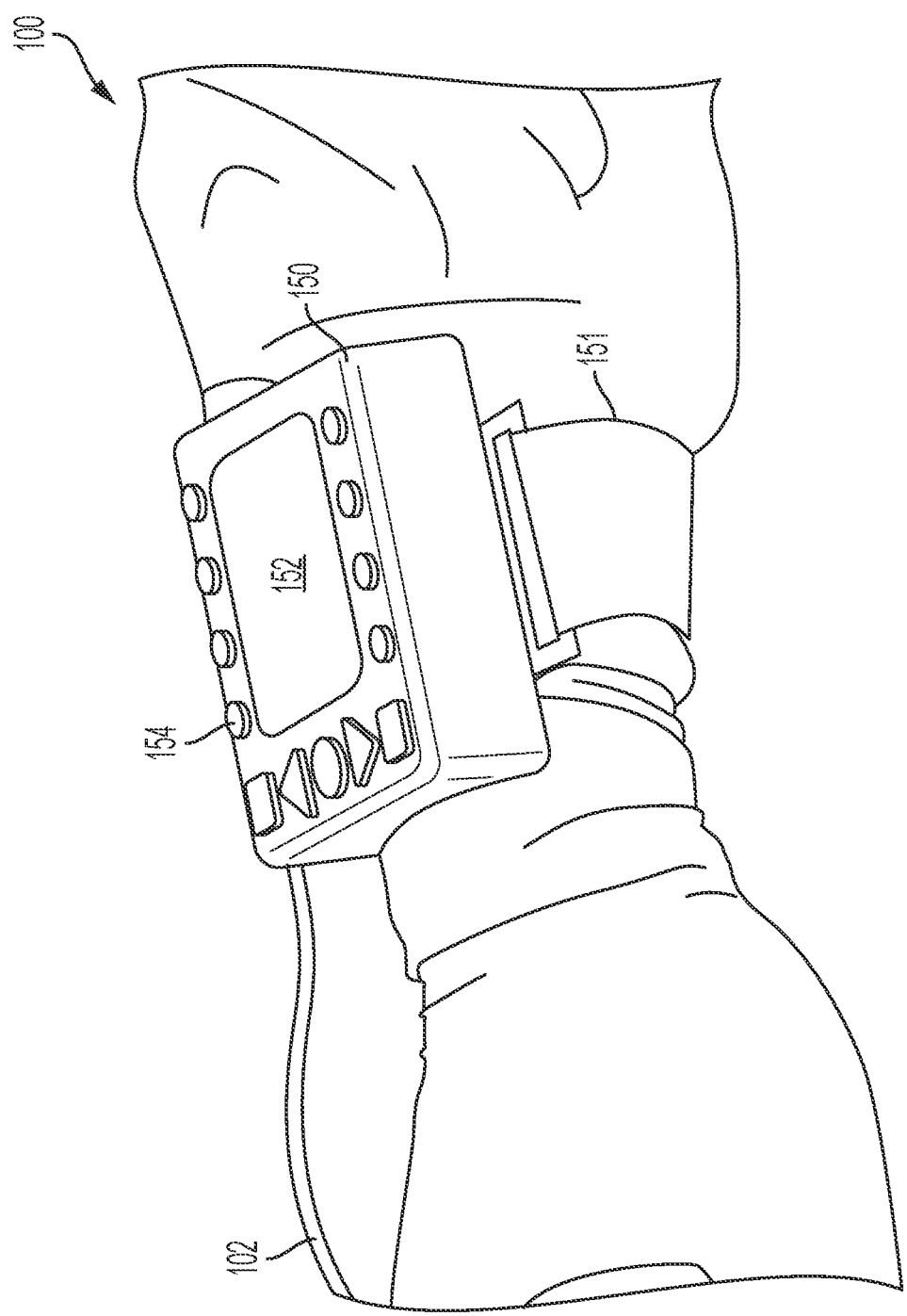
FIG. 1 illustrates an example drug delivery system.

FIG. 1 illustrates an example drug delivery system 100. The system 100 includes a a wearable micropump 150. The wearable micropump 150 is coupled to a handpiece 104, which is not shown in FIG. 1, via tubing 102. The wearable micropump 150 can be worn on the wrist or lower arm of the user.

The system 100 is configured to deliver drug, therapeutic agents, fluids, or other materials to a human's natural cavities. The injected substances can generally be referred to as fluids. The cavities can include, but are not limited to, the inner ear, ocular cavity, spinal cavity, oral cavity, anal cavity, urinary cavity, and/or cervix cavity. The system 100 can control the level of drug penetration, amount of drug diffusion, volume of drug injected, and the flow rate of the injected drug. The system 100 can include a wearable micropump which includes a user interface via which one or more settings of the wearable micropump are settable. The wearable micropump includes one or more selectable buttons via which one or more settings of the wearable micropump are settable.

The system 100 includes tubing 102 for the delivery of the drug to the body cavity (e.g., via a handpiece). The system 100 also includes a wearable micropump 150. The wearable micropump 150 is a small, wearable, self-contained pump. The wearable micropump 150 can be self-contained by internally including a power system to power the pump and one or more reservoirs to store the fluid to be injected. The wearable micropump 150 includes a strap 151 that enables the wearable micropump 150 to be worn on the wrist, arm, or hand of the user. Wearing the wearable micropump 150 can bring the wearable micropump 150 close to a handpiece 104. The proximity of the wearable micropump 150 to the handpiece 104 can limit the amount of dead volume within the tubing 102 between the wearable micropump 150 and the handpiece 104. The dead volume can be greater than or equal to 1 microliter and less than or equal to 75 microliters. The dead volume can correspond with a distance of 150 millimeters through the tubing 102 (e.g., a distance greater than or equal to 100 millimeters and less than or equal to 200 millimeters) and an inner diameter of 0.79 millimeters (e.g., an inner diameter greater than or equal to 0.1 millimeters and less than or equal to 0.8 millimeters). The proximity of the wearable micropump 150 to the handpiece 104 can also improve the precision and control of drug penetration, drug diffusion, volume injection, and flow rate.

The wearable micropump 150 can include a display 152 to display to the wearer the status of the wearable micropump 150 and information about the status of the delivery of the fluid to the patient. The wearable micropump 150 can include a plurality of inputs 154, such as buttons, that the wearer can use to control the delivery of the drug to the patient.

Figure 2:
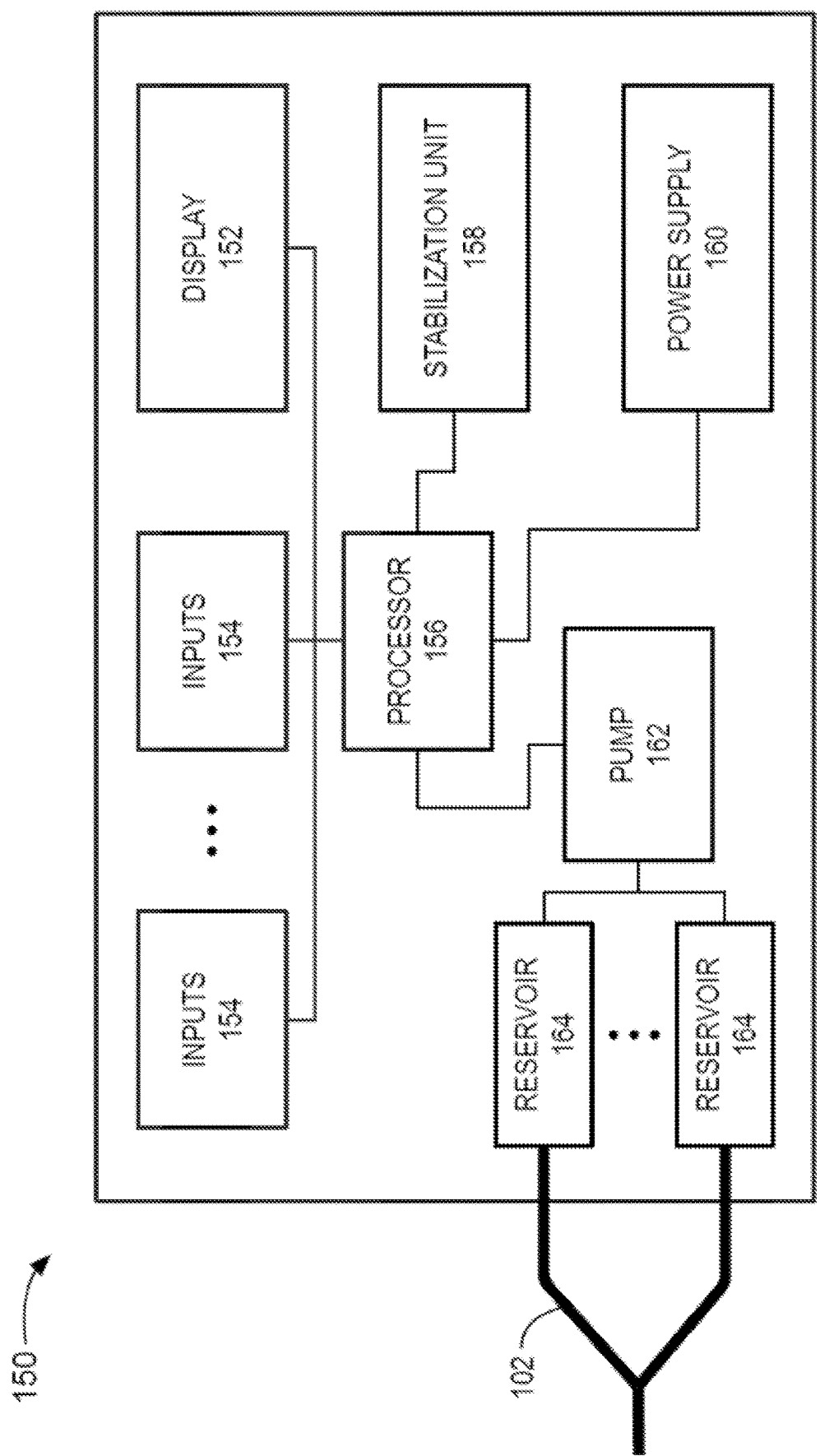
FIG. 2 illustrates an example schematic of the wearable micropump for use in the system illustrated in FIG. 1.

The wearable micropump 150 is described in greater detail in relation to FIG. 2, among others. The handpiece 104 is described in greater detail in relation to FIG. 3.

FIG. 2 illustrates an example schematic of the wearable micropump 150. The wearable micropump 150 can include a display 152. The wearable micropump 150 can include a plurality of inputs 154 to control the wearable micropump 150. The wearable micropump 150 can include a processor 156 to control the function of the wearable micropump 150. The wearable micropump 150 can include a stabilization unit 158 to stabilize hand movements of the wearable micropump 150. The wearable micropump 150 can include a pump 162 and one or more reservoirs 164 to deliver fluids to the handpiece 104 via the tubing 102.

The wearable micropump 150 can include a plurality of inputs 154. The inputs 154 can be buttons, knobs, or other types of interfaces of the wearable micropump 150. The inputs 154 can be physical inputs, such as physical buttons positioned on a housing or face of the wearable micropump 150. The inputs 154 can be virtual inputs. For example, the display 152 can be touch sensitive and the virtual buttons can be selectable buttons that are displayed on the display 152. The inputs 154 can be coupled within input pins of the processor 156.

Via the inputs 154, the user can navigate the interface of the wearable micropump 150 to, for example, determine the status of the wearable micropump 150 and select injection parameters. The status of the wearable micropump 150 can include an amount of remaining fluids in the reservoirs 164, an amount of fluids delivered via the wearable micropump 150, current power level of the power supply 160, or status of the stabilization unit 158 (e.g., active or inactive). The injection parameters can include fluid injection rate, total allowed fluid injection volume, selection of which fluid to inject, the sequence or order of fluid injection, and withdrawal rate.

The wearable micropump 150 can include a display 152. Via the display 152, the wearable micropump 150 can display injection parameters and wearable micropump 150 status information to the wearer. The display 152 can be touch sensitive to enable selectable buttons to be displayed and selected via the display 152.

The wearable micropump 150 can include a processor 156. The processor 156 can be any type of single or multi-core processor or special purpose logic circuitry such as an FPGA (field programmable gate array) or an ASIC (application specific integrated circuit). In some implementations, the processor 156 can include one or more antennas to enable the processor 156 (and wearable micropump 150) to communicate with external devices. For example, the processor 156 can communicate with an external controller or remote that can be used to start, stop, or pause the flow of fluid to the handpiece 104. The external controller or remote can be operated by a second user other than the user wearing the wearable micropump 150.

The wearable micropump 150 can include a stabilization unit 158. The stabilization unit 158 can stabilize the wearable micropump 150 and counteract tremors or other involuntary hand movements that can cause undesired movement of the handpiece 104. The stabilization unit 158 can include accelerometers that can detect the movement of the wearable micropump 150 and handpiece 104. The stabilization unit 158 can include a plurality of gyroscopes that, when activated, can spin to provide stability to the wearable micropump 150 and counteract movements of the wearable micropump 150 and handpiece 104.

The wearable micropump 150 can include a power supply 160. The power supply 160 can include rechargeable batteries or capacitor that can supply power to the components of the wearable micropump 150. The power supply 160 can include batteries that are not rechargeable. For example, the power supply 160 can be a plurality of batteries that can be removed and replaced once the power of the batteries is consumed. In some implementations, the power supply 160 can include an alternating current (AC) to direct current (DC) converter. For example, the wearable micropump 150 can be plugged into an AC mains. The power supply 160 can convert the power from the AC mains into DC power that can be used by the processor 156 and other components of the wearable micropump 150.

The wearable micropump 150 can include one or more pumps 162. The wearable micropump 150 can include a single pump 162. The single pump 162 can selectively drive fluid from each of the reservoirs 164. For example, the processor 156 can set the state of one or more valves that enable the single pump 162 to flow fluid from one reservoir 164 (or a portion of the total number of reservoirs 164) to the tubing 102.

The wearable micropump 150 can include a plurality of pumps 162. For example, the wearable micropump 150 can include a different pump 162 for each of the reservoirs 164. Each of the different pumps 162 can be the same type of pump or a different type of pump. The pump 162 can include one or more of a lead screw-driven mini syringe pump, 3-actuator micropump, mini peristaltic pump, or pneumatic/hydraulic-driven pump. The pneumatic/hydraulic-driven pump can be driven by an external pressure source that can be coupled with the wearable micropump 150 to drive the pump 162. In some implementations, different configurations of the wearable micropump 150 with different pumps types can be selected based on the drug or fluid within the reservoirs 164. For example, a first pump type can be used for fluids with a relatively high viscosity and a second pump type can be used for fluids with a relatively low viscosity. In some implementations, one or more pumps 162 can withdraw a fluid from the cavity. These pumps 162 can be referred to as vacuum pumps. The pumps 162 can withdraw the fluid into a separate reservoir 164 configured to store the withdrawn fluid.

The processor 156 can receive an instruction to set or update one or more settings from the inputs 154. For example, the processor can control operation of the pumps 162 or other components of the wearable micropump 150 according to the settings. The processor 156 can maintain the settings in memory. The processor 156 can maintain default values for the settings in memory, which can be updated based on the received instructions. The processor 156, responsive to receiving the instruction, can modify operation of the pumps 162 responsive to updating the one or more settings. The modification of the operation of the pump 162 can include modifying the state of one or more valves that enable the single pump 162 to flow fluid from a reservoir 164 to a tubing 102. The processor 156 can receive input from a stabilization unit 158 to monitor the state of the stabilization unit 158 (e.g., via accelerometers and gyroscopes). The processor 156 can use DC power from a power supply 160 to drive pumps 162, and can control flow rates or other parameters of the pumps 162 based on the updated settings (e.g., by controlling power used to drive pumps 162 from power supply 160). The processor 156 can use a lookup table or a function or correlation between a value indicated by the instruction and the one or more settings maintained in memory to update the one or more settings.

In some implementations, the vacuum pump can be an independent pump that is configured to only withdraw fluid from the cavity. In some implementations, the pumps 162 can be configured to operate in multiple directions such that during a first time period or phase the pumps 162 can pump fluid into the cavity, and during a second time period or phase the pumps 162 can withdraw fluid from the cavity. In some implementations, a first pump acting as a vacuum pump can operate at the same time as a second pump flows fluid into a cavity such that the amount of fluid removed by first pump is substantially the same as the amount of fluid injected by the second pump.

The wearable micropump 150 can include one or more reservoirs 164. The reservoirs 164 can include a drug to be delivered to the patient via the handpiece 104. The drug can be generally referred to as a fluid. The drug can be a gel. The fluid can be a two-part gel. For example, a first part of the gel can be stored in a first reservoir, and a second part of the gel can be stored in a second reservoir. The fluid can include large molecules such as proteins, antibodies, genes, DNA, RNA, particles, viruses, liposomes, nanoparticles, microspheres, and magnetic drug delivery particles. Each fluid in the different reservoirs 164 can be the same or different fluids. In some implementations, one or more reservoirs 164 can be initially empty, and the pump 162 can be used to draw fluid from the patient which can be stored in the reservoirs 164.

In some implementations, the reservoirs 164 can be removable from the wearable micropump 150. For example, each reservoir 164 can be a vial that includes a pierceable septum. The wearable micropump 150 can include receptacles for the vials. Each receptacle can include a needle that can pierce the septum of the vial when the vial is pressed into the receptacle. The needle can pass through the septum and into the vial to withdraw the fluid from the vial. In some implementations, once a vial is empty the vial can be removed and a new vial (with additional fluid) can be placed into the receptacle to enable additional fluid to be delivered to the patient.

In some implementations, the reservoirs 164 can include a pierceable septum to enable fluid to be loaded into the reservoirs 164. Via the pierceable septum, the reservoir 164 can be accessed. For example, a user can draw a fluid into a syringe. The user can pierce the septum to inject the fluid from the syringe and into the reservoir 164.

Each reservoir 164 can include a window or be manufactured from a clear material. The window can enable the operator of the system 100 to visualize the amount of fluid remaining in each reservoir 164 during or after an injection phase. In some implementations, each reservoir 164 can include graduated markings so the volume of fluid in the reservoir 164 can be visualized. In some implementations, the housing of the wearable micropump 150 can include a window to enable visualization of the reservoir 164 or window of the reservoir 164 once the reservoir 164 is inserted into the wearable micropump 150.

Each reservoir 164 can be fluidically coupled with the tubing 102 that couples the wearable micropump 150 with the handpiece 104. In some implementations, each reservoir 164 can be fluidically coupled with the handpiece 104 via a separate tubing 102. Each of the tubes 102 can be bound or coupled together to ease in the management of the tubes 102. In some implementations, the tube 102 can include a plurality of different internal lumens, and each of the reservoirs 164 can be coupled with a different lumen.

Figure 3:
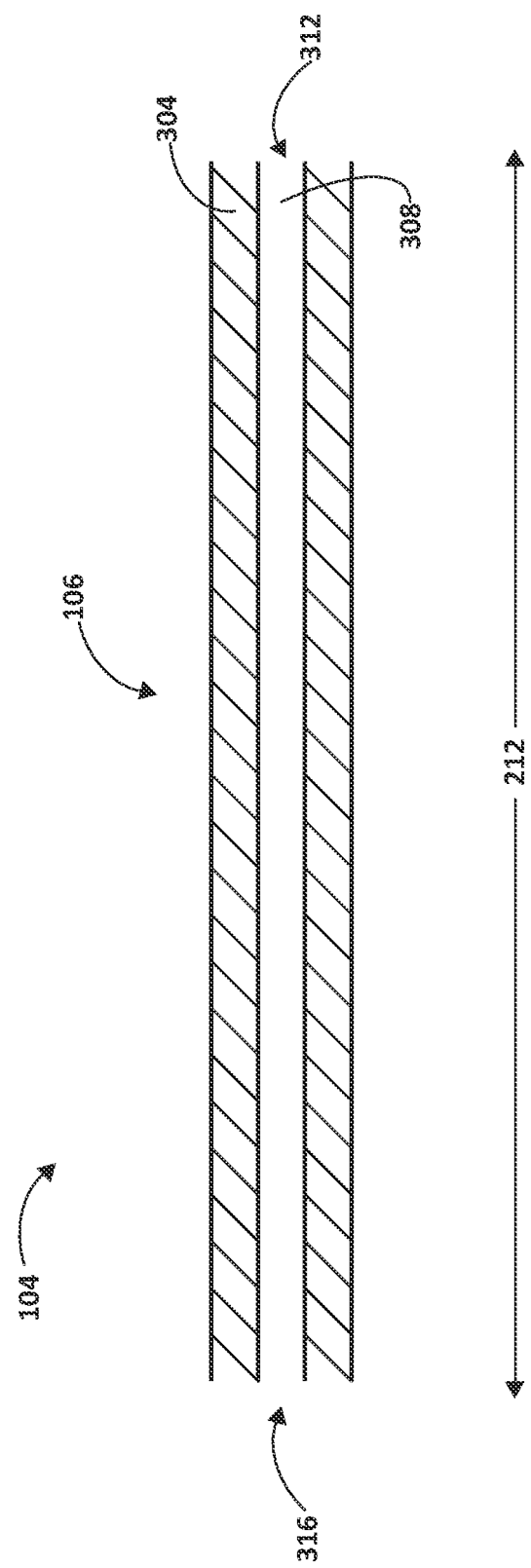
FIG. 3 illustrates a side view of the example handpiece illustrated in FIG. 1.

FIG. 3 illustrates a side view of an example handpiece 104 for delivering fluid to a patient's cavity such as the inner ear. The fluid can be any therapeutic substance or therapeutic agent. The handpiece 104 includes a tool shaft 106 and a tip portion 316. The tip portion 316 can be used to pierce membranes or other thin tissue. For example, the handpiece 104 can be inserted into the ear canal of the patient for the transcanal delivery of fluid to the cochlea via the round window. The tip portion 316 can be used to pierce the round window membrane to enable fluid, flowing through the handpiece 104 and the channel 308, to be delivered to the cochlea.

A surgeon can use the tool shaft 106 to hold and manipulate the handpiece 104 and position of the tip portion 316. The outer surface of the tool shaft 106 can include features, such as knurling, to enable a better grip of the handpiece 104 by the surgeon. The tool shaft 106 includes a proximal end 312 and can have various diameters, such as a diameter of about 4 mm, 5 mm, or about 6 mm. The tool shaft 106 can have various lengths, such as a length of between about 90 mm and about 150 mm, between about 90 mm and about 130 mm, or between about 100 mm and about 120 mm. The handpiece 104 can have various shapes and form factors, such as various angled portions, multiple channels 308, and a collar at the tip portion.

The handpiece 104 can have various lengths, such as an overall length 212 between about 130 mm and about 170 mm, between about 140 mm and about 160 mm, or between about 140 mm and about 150 mm. While described as different portions, the tool shaft 106 and the tip portion 316 can each be manufactured as single or multiple pieces. For example, the handpiece 104 can include one, two, or three separate pieces. The handpiece 104 can be separable at the interface between any of the tool shaft 106 and the tip portion 316. In some implementations, the interface between the tool shaft 106 and the tip portion 316 does not indicate that the portions are separable. For example, the tool shaft 106 and the tip portion 316 can be manufactured as a single piece. In other implementations, the tool shaft 106 can form a first piece and the tip portion 316 can form a second piece. In some implementations, the handpiece 104 is reusable. In other implementations, the handpiece 104 is disposable. The handpiece 104 can be manufactured from medically-approved sterilizable materials. For example, the handpiece 104 can be manufactured from 304 stainless steel or a sterilizable plastic.

Figure 4:
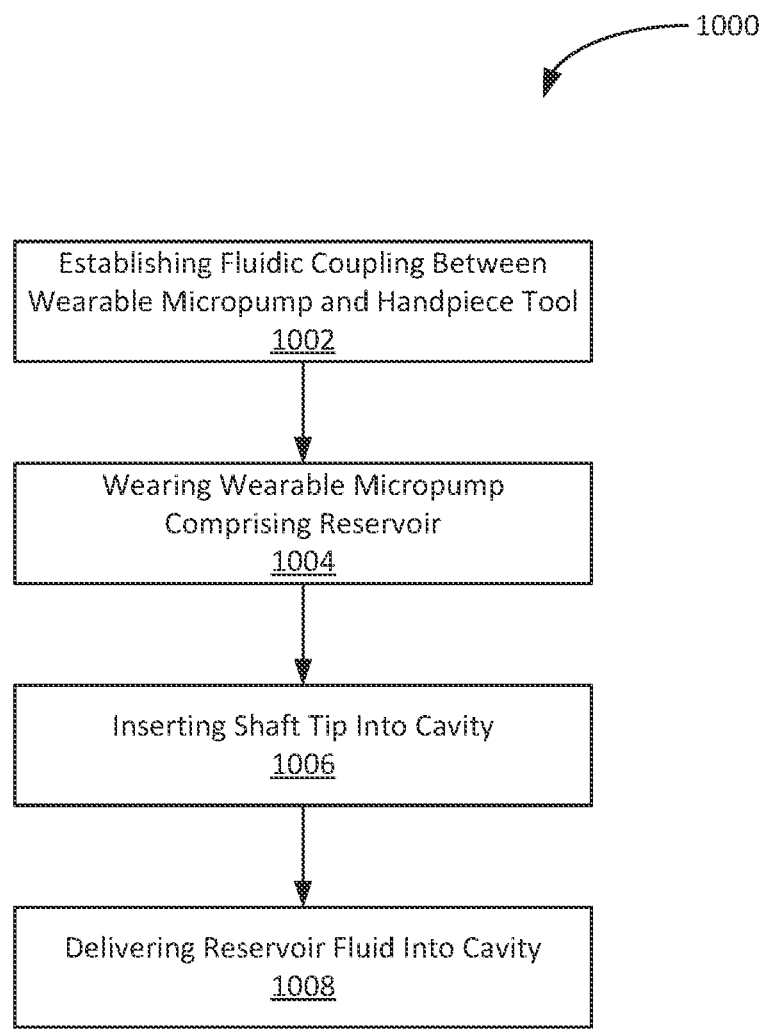
FIG. 4 illustrates a block diagram of an example method to flow a fluid into the cochlea with the system illustrated in FIG. 1.

FIG. 4 illustrates a block diagram of an example method 1000 to flow a fluid into the cochlea. The method 1000 can include establishing fluidic coupling between a wearable micropump and a handpiece tool (1002). The method 1000 can include wearing a wearable micropump comprising a reservoir (1004). The method 1000 can include inserting a shaft tip into a cavity (1006). The method 1000 can include delivering reservoir fluid into a cavity (1008).

As set forth above, the method 1000 can include establishing fluidic coupling between a wearable micropump and a handpiece tool via a tubing connected between a port of the wearable micropump and an end of a shaft of the handpiece tool having a microfluidic channel (1002). Also referring to FIGS. 1-3, the system 100 can include a wearable micropump 150 that is coupled with a handpiece 104 to flow fluid through the handpiece 104 and out an outlet of the handpiece 104.

The wearable micropump 150 can include one or more reservoirs 164 that each can include a different fluid. The fluid can be a therapeutic, drug, or other active agent. The wearable micropump 150 can include one or more pumps that flow the fluid from the reservoirs 164 to the handpiece 104 via a tubing 102.

The handpiece 104 can be any of the handpieces described herein. For example, the handpiece 104 can include a tool shaft that includes a first distal end, a first proximal end, a first fluidic channel, and a first longitudinal axis.

The method 1000 can include wearing, by a wearer, the wearable micropump comprising a reservoir through a port connectable to the tubing 102 (1004). The wearable micropump 150 can include a strap 151 that can be attached to the wearable micropump 150 to enable the wearable micropump 150 to be worn on the wrist, arm, or hand of the user. When worn, wearable micropump 150 can bring the wearable micropump 150 close to a handpiece 104 for use on a patient. The wearable micropump 150 can include one or more reservoirs for the purpose of holding fluid. A wearable micropump can include a pump for managing the flow of the fluid from the reservoir to the handpiece 104. The wearable micropump 150 can include a connectable port to connect the reservoir to the tubing 102 for the pump to easily flow fluid through the reservoir and into the tubing 102 and handpiece 104.

The method 1000 can include inserting, by a wearer, a tip of the shaft of the handpiece tool into a cavity of a patient (1006). The round window membrane can be pierced with the tip portion of the handpiece 104. For example, the provided handpiece 104 can be inserted through the ear canal.

As described above, a method similar to the method 1000 can be performed to inject a fluid into other cavities of a patient. In some implementations, the system can be used to inject fluids into an ocular cavity. For example, the handpiece tip can be inserted into the inferior temporal quadrant 3.5 mm posterior to the limbus and a drug from the system's reservoirs 164 can be injected into the vitreous cavity. After retracting the tip of the handpiece 104, the transcleral perforation can be closed with a 50-μm-thick cyanoacrylate bioadhesive-fixed polyimide patch.

In some implementations, the system 100 can be used to inject fluids into a spinal cavity. The system 100 can be used to deliver drugs into the epidural space via the interlaminar, caudal, or transforaminal approach. During the interlaminar approach, the handpiece tip can be placed into the back of the epidural space and the drug can be delivered over a wider area. During the caudal approach, the sacral hiatus can be used to enable the handpiece tip to be placed into the very bottom of the epidural space. Once injected, the drug can spread over several spinal segments and cover both sides of the spinal canal. During the transforaminal approach, the handpiece tip can be placed alongside the nerve as it exits the spine and the fluid can be injected into the "nerve canal." The fluid can then travel up the nerve canal and into the epidural space from the side. This method can enable for a more concentrated delivery of the fluid into one affected area.

In some implementations, the system 100 can be used to inject fluids into a rectal cavity. During rectal surgery, the handpiece tip can be inserted into the rectal cavity to reach the rectal mucosa. Upon insertion of the handpiece tip into the mucosa, fluid can be delivered and the handpiece can be retracted. Areas nearby pathological tissue can be injected to limit spreading of the disease.

In some implementations, the system 100 can be used to inject fluid into the nasal cavity. For example, the drug can be injected into the bilateral maxillary sinus by inserting the handpiece tip into the superior meatus location of the olfactory epithelium. After reaching the area near the olfactory epithelium, a gel can be injected via the handpiece 104 that will release the gel's drug directly into the brain.

In some implementations, the system 100 can be used to inject fluids into the vaginal cavity. During cervical surgery, the handpiece tip can be inserted into the cervix cavity. Areas nearby cancerous tissue can be injected with the insertion of the handpiece tip to deliver fluids adjacent to the cancerous tissue either before resection (to reduce tumor size) or after resection (to reduce the risk of recurrence). Prior to the drug delivery, contrast dye can be used to confirm that the medication is traveling into the desired area.

The method 1000 can include delivering, via the wearable micropump responsive to the pump and while being worn by the wearer, fluid from the reservoir through the tubing 102 through the microfluidic channel of the handpiece tool through an outlet of the tip of the handpiece tool to the cavity of the patient (1008). A pump of the wearable micropump 150 can pump the fluid from a reservoir 164, through the microfluidic channel 300, and into the cochlea via outlet 304. The method 1000 can include drilling, or otherwise forming, a ventilation hole in the stapes footplate. The ventilation hole can enable the release of pressure from the cochlea as the pump flows the fluid into the cochlea. In some implementations, the method 1000 can include withdrawing a fluid from the cochlea as fluid is pumped into the cochlea to maintain a constant pressure within the cochlea.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A method for using a wearable micropump with a handpiece tool to deliver a fluid to a patient, the method comprising:
 establishing a fluidic coupling between a wearable micropump and a handpiece tool via a tubing connected between a port of the wearable micropump and an end of a shaft of the handpiece tool having a microfluidic channel;
 wearing, by a wearer, the wearable micropump comprising a reservoir configured to hold a fluid and a pump configured to flow the fluid from the reservoir through the port;
 inserting, by the wearer, a tip of the shaft of the handpiece tool into a cavity of a patient;
 operating a stabilizer comprising at least one of an accelerometer or a gyroscope, the stabilizer coupled with the housing; and
 delivering, via the wearable micropump responsive to the pump and while being worn by the wearer, fluid from the reservoir through the tubing through the microfluidic channel of the handpiece tool through an outlet of the tip of the handpiece tool to the cavity of the patient.

2. The method of claim 1, further comprising activating, by the wearer, the wearable micropump to deliver fluid while the tip of the shaft of the handpiece tool is projected into the cavity of the patient.

3. The method of claim 1, further comprising wearing, by the wearer, the wearable micropump on a wrist.

4. The method of claim 1, further comprising setting, by the wearer, one or more settings of the wearable micropump via an interface of the wearable micropump while wearing the micropump.

5. The method of claim 1, further comprising setting, by the wearer, one or more settings of the wearable micropump via an interface of the wearable micropump while delivering fluid via the tip of the shaft of the handpiece tool into the cavity of the patient.

6. The method of claim 1, further comprising stabilizing, by the stabilizer, the wearable micropump.

7. The method of claim 1, further comprising presenting, by an interface of the wearable micropump, a status of the wearable micropump.

8. The method of claim 1, wherein the pump comprises a plurality of pumps.

9. The method of claim 8, further comprising operating a first pump of a first type of the plurality of pumps to deliver a first fluid having a first viscosity and operating a second pump of a second type of the plurality of pumps to deliver a second fluid having a second viscosity less than the first viscosity.

10. The method of claim 1, further comprising selecting a fluid to inject using the pump responsive to a selection of the fluid received at an interface of the wearable micropump.

11. The method of claim 1, further comprising controlling operation of the wearable micropump based at least on a signal from a remote device.

12. The method of claim 1, further comprising withdrawing fluid from the cavity of the patient.

13. The method of claim 12, further comprising withdrawing fluid from the cavity of the patient while pumping fluid into a cochlea of the patient to maintain a constant pressure within the cochlea.

* * * * *